United States Patent
Kalbfleisch et al.

(10) Patent No.: US 6,589,510 B2
(45) Date of Patent: Jul. 8, 2003

(54) VOLUME-IMPARTING HAIR TREATMENT PRODUCT FOR STRENGTHENING THE HAIR SHAFT

(75) Inventors: Axel Kalbfleisch, Darmstadt (DE); Susanne Birkel, Darmstadt (DE); Michael Lede, Langen (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/992,093

(22) Filed: Nov. 6, 2001

(65) Prior Publication Data

US 2002/0090346 A1 Jul. 11, 2002

(30) Foreign Application Priority Data

Nov. 10, 2000 (DE) .......................................... 100 55 935

(51) Int. Cl.$^7$ .................................................. A61K 7/06
(52) U.S. Cl. ................. 424/47; 424/70.122; 424/70.15; 424/70.16; 424/70.17
(58) Field of Search .............................. 424/47, 70.122, 424/70.15, 70.16, 70.17

(56) References Cited

U.S. PATENT DOCUMENTS 6,042,819 A * 3/2000 Karlen et al. ............. 424/78.17
6,383,477 B1 * 5/2002 Lede et al. ............... 424/70.15

FOREIGN PATENT DOCUMENTS

WO        99/67216        12/1999

OTHER PUBLICATIONS

RD 422068 Abstract (Jun. 1999).*

* cited by examiner

*Primary Examiner*—Jyothsan Venkat
(74) *Attorney, Agent, or Firm*—Michael J. Striker

(57) ABSTRACT

A hair treatment product and method for imparting volume to a hairdo or for strengthening the hair shafts of the hairdo is provided. The hair treatment product is a pressure-resistant aerosol container containing a composition, which forms fast-breaking foam on a section of the hairdo including the hair shafts by means of a spraying head having a comparatively narrow spraying angle. The composition in the aerosol container includes at least 60 percent by weight of water; from 1 to 30 percent by weight of $C_1$- to $C_5$-monovalent alcohol as a foam-breaking agent; from 0.01 to 5 percent by weight of a foam-forming surfactant; from 0.1 to 20 percent by weight of at least one hair-fixing polymer; and an aerosol propellant.

14 Claims, No Drawings

VOLUME-IMPARTING HAIR TREATMENT PRODUCT FOR STRENGTHENING THE HAIR SHAFT

BACKGROUND OF THE INVENTION

The subject matter of the present invention is a hair treatment product, with which it is possible to strengthen the hair shaft and to impart volume to a particular hair-do or hairstyle. This product includes an aqueous, polymeric and surfactant-containing composition, from which foam is produced when the product is used by means of an aerosol propellant. However this product includes an aerosol container for the composition, which is equipped with a spray head instead of a foam head, so that very rapidly breaking unstable spray foam is formed from the composition in use.

Hair treatment compositions in aerosol form are generally divided into two groups: aerosol hair sprays and aerosol hair foams. The aerosol hair sprays are sprayed on the entire hair-do or hairstyle and thus the hair-do or hairstyle is fixed or set. It is not possible to separately style individual sections of the hair. Aerosol foams are first applied to the hand and then subsequently distributed on the hair with the hand. Also a desired treatment of individual sections of the hair is not possible with aerosol foams. Moreover the treated hair is wet over its entire length with a polymer-containing composition during application of conventional aerosol foams and sprays. The hair no longer feels natural because of the presence of the polymer-containing composition on it. The feel of the hair is then determined by the nature of the polymer film on the hair. This polymer film produces a notable negative impression, especially on fine hair. Frequently observed additional undesirable side effects include a rough feel of the treated hair, a high load on the hair, insufficient elasticity of the treated hair and a visible residue formed on the treated hair.

SUMMARY OF THE INVENTION

It is an object of the present invention to make it possible to impart more volume and to fix individual sections of the hair, without loading the hair or imparting an unnatural feel to the hair.

It has now been found that this object is attained by a hair treatment product for strengthening the hair shaft, which includes a pressure-resistant aerosol container with a hair spray head and a composition contained in the aerosol container. This composition forms rapidly breaking, unstable foam when it is sprayed. This composition comprises (A) at least 60 percent by weight, water;
(B) at least one foam-breaking agent;
(C) at least one surfactant;
(D) at least one hair-fixing polymer with strong hair-fixing properties, which is selected from those hair-fixing polymers that provide a higher curl retention than polyvinyl pyrrolidone, measured after 23 hours at 20° C. and 85% relative humidity; and
(E) at least one aerosol propellant.

When a spray head with a narrow spray angle is selected it is possible to spray the composition in the product of the invention on the hair shafts. Thus unstable foam is produced on the hair shaft, which can act as a temporary indicator for the treated hair section. The foam breaks on the hair shafts rapidly, without working it in the hair, i.e. without contact by the hands, as is the case with conventional hair foams. The foam breaking is advantageously accelerated using a hair drier.

Hair-fixing Polymer

A strongly fixing hair-fixing polymer is used as component (D) of the composition. Polymers, which provide an especially strong fixing of the hair, frequently have the disadvantage that they impart an unnatural, stiff and rough feel to the hair, when they are used in a conventional hair spray or foam and thus are applied usually to the entire hair. These kinds of polymers however are especially suitable in the products according to the invention. Since the volume effect is exclusively produced by fixing the hair shafts, i.e. by fixing a relatively small part of the hair in the vicinity of the scalp, there are special requirements for the quality of the fixing and/or the polymer film produced by it. Otherwise, if these requirements are not met, the remaining part of the hair strands act like a quasi-lever and the desired effect is not produced. Thus particularly polymers, which form an especially strong inflexible or rough film, are especially suitable, i.e. those polymers which are disadvantageous in conventional hair sprays.

Those polymers which have a stronger fixing action than the standard fixing polymers, polyvinyl pyrrolidone or vinyl pyrrolidone/vinyl acetate copolymer, are especially suitable as the strongly fixing hair-fixing polymers in the product according to the invention. The fixing strength is determined by measuring curl retention after 23 hours at 20° C. and 85% relative humidity. Polymers, which have about at least 20%, especially about at least 40%, curl retention in comparison to untreated hair, under the foregoing conditions are especially preferred.

The fixing polymers (D) are used in an amount of preferably from 0.1 to 20, especially preferably from 1 to 5, percent by weight.

Suitable hair-fixing polymers are, for example, polymers, which are made by the process described in W 99/67216. These polymers contain repeating units of alpha-olefin N-alkylmaleimide or alph-olefin N-hydroxyalkylmaleimide. An imidated poly(isobutylen-co-maleic acid anhydride), a polymer with the INCI name, isobutylene/ethylmaleimide/hydroxyethylmaleimide copolymer, is especially suitable. AQUAFLEX® FX-64 of ISP is an especially suitable commercial product.

Suitable fixing polymers also include amphoteric copolymers, formed from alkylacrylamides, alkylaminoalkylmethacrylates and two or more monomers selected from the group consisting of acrylic acid, methacrylic acid or their esters, of which at least one of the monomers contains an acid group. The alkyl groups can contain from 1 to ten carbon atoms. The copolymer formed from octylacrylamide, t-butylaminoethylmethacrylate and two or more monomers selected from the group consisting of acrylic acid, methacrylic acid or their esters, of which at least one of the monomers contains an acid group, which has the INCI name, octylacrylamide/acrylate/butylaminoethylmethacrylate copolymer, is particularly preferred. AMPHOMER® or AMPPHOMER® LV-71 of National Starch Co. is an especially suitable commercial product.

Additional suitable polymers include copolymers of vinylpyrrolidone and quaternary dialkylaminoalkylacrylates. The alkyl groups can contain from one to four carbon atoms. A copolymer formed from vinylpyrrolidone and quaternarized dimethylaminoethylmethacrylate, which has the INCI name Polyquaternium 11, is especially suitable. GAFQUAT® 755 N of ISP or LUVIQUAT® PQ11 of BASF are especially suitable commercial products.

Copolymers of vinyl acetate and crotonic acid with the INCI name VA/crotonate copolymer are also suitable for the composition of the invention. LUVISET® CA66 of BASF is a suitable commercial product.

Copolymers of acrylamides and one or more monomers selected from the group consisting of acrylic acid, methacrylic acid and their simple esters, especially $C_1$- to $C_4$-alkyl esters, are also additional suitable polymers. At least one monomer of these polymers should contain a carboxylic acid group. Preferred acrylamides include N—$C_1$- to $C_4$-alkylacrylamides, which have the INCl name acrylates/acrylamide copolymer. An acrylic acid/ethylacrylate/N-tert.-butyl-acrylamide terpolymer is especially preferred. ULTRAHOLD® 8 of BASF is a suitable commercial product.

Terpolymers of vinyl pyrrolidone, vinyl caprolactam and a basic acrylamide monomer, preferably dialkylaminoalkylmethacrylmaide, in which the alkyl group have from 1 to 4 carbon atoms, are additional suitable polymers. A vinylpyrrolidone/vinylcaprolactam/dimethylaminopropylmethacrylamide terpolymer is particularly preferred. AQUAFLEX® SF40 of ISP, which has the INCl name PVP/vinyl caprolactam/DMAPA acrylates copolymer, is a suitable commercial product.

Additional suitable polymers include copolymers of two or more different monomers selected from the group consisting of acrylic acid, methacrylic acid and their simple esters, especially $C_1$- to $C_4$-alkyl esters. At least one monomer should contain an acid group. The INCl name of this polymer is acrylates copolymer. A t-butylacrylate/ethylacrylate/methylacrylic acid terpolymer is preferred. LUVIMER® 100P of BASF is a suitable commercial product.

Surfactants

At least one surfactant, preferably a foam-forming surfactant, is contained in the composition in the product of the invention as component (C). Foam-forming surfactants are those surfactants, which produce a foam height of at least 1 cm in a Ross-Miles test performed at 20° C. The surfactant can have nonionic, anionic, cationic or amphoteric character. Nonionic, foam-forming surfactants are especially preferred. The at least one surfactant can consist of a single surfactant or a mixture of two or more surfactants. The amount of the surfactants can vary and is selected so that a portion of sufficient size for the particular application forms quick-breaking foam, when the composition is dispensed from the aerosol container. The surfactant quantity is typically from 0.01 to 5, preferably from 0.1 to 2, percent by weight.

Suitable nonionic surfactants are, for example, $C_8$- to $C_{18}$-fatty alcohols, which are ethoxylated with 3 to 45 Mol ethylene oxide, e.g. stearyl alcohol, oleyl alcohol, cetyl alcohol, tetradecyl alcohol or lauryl alcohol ethoxylated with up to 40 Mol ethylene oxide per molecule of fatty alcohol, alone or in a mixture; ethoxylated castor oil hydrogenated with 8 to 45 Mol ethylene oxide, $C_8$- to $C_{18}$-fatty acid alkanol amides; fatty alcohols of ethoxylated lanolin or ethoxylated lanolin; polyglyceryl ethers of saturated or unsaturated fatty alcohols and alkyl phenols with 8 to 30 carbon atoms in their alkyl groups and 1 to 10 glyceryl units in the molecule; polyethylene/propylene block copolymers and ethoxylated sorbitan fatty acid esters. Moreover alkylpolyglycosides, which have alkyl group with eight to eighteen carbon atoms, are especially preferred as the nonionic surfactants.

Suitable anionic surfactants include, e.g., alkyl sulfates, alkyl ether sulfates, alkyl sulfonates, alkoylsarcosinates, alkylisethionates or dialkylsulfosuccinates, wherein the alkyl groups can contain from 8 to 18 carbon atoms.

Suitable amphoteric surfactants include those of the betaine type. These betaines include $C_8$- to $C_{18}$-alkylbetaines, such as coconut dimethylcarboxymethylbetaine, lauryldimethylcarboxymethylbetaine, lauryldimethylalpha-carboxyethylbetaine, cetyldimethylcarboxymethylbetaine, oleyldimethyl-gamma-carboxybetaine and lauryl-bis-(2-hydoxypropyl)alpha-carboxyethylbetaine; $C_8$- to $C_{18}$-sulfobetaines, lauryl-bis-(2-hydoxyethyl)-sulfopropylbetaine; carboxyl derivatives of imidazoles, which include $C_8$- to $C_{18}$-alkyldimethylcarboxymethylammonium salts as well as the $C_8$- to $C_{18}$-fatty acid alkylamidobetaines, such as coconut fatty acid amidopropylbetaine and N-coconut fatty acid amidoethyl-N-[2-(carboxymethoxy)ethyl]glycerol (CTFA name: cocoamphocarboxyglycinate).

Suitable cationic surfactants include surfactants, which contain quaternary ammonium groups. Suitable cationic surfactants can be of the general formula (I):

$$N^{(+)}R^1R^2R^3R^4 \ X^{(-)} \qquad (I),$$

wherein $R^1$, $R^2$, $R^3$ and $R^4$, independently of each other, are aliphatic groups, aromatic groups, alkoxy groups, polyoxyalkylene groups, alkylamido groups, hydroxyalkyl groups, aryl groups or alkaryl groups with from 1 to 22 carbon atoms, with the proviso that at least one of the $R^1$, $R^2$, $R^3$ and $R^4$ groups have at least eight carbon atoms, and $X^{(-)}$ is an anion. For example, the anion can be halogen, acetate, phosphate, nitrate or alkyl sulfate, preferably a chloride. The aliphatic groups can also contain cross-linking groups or other groups, for example amino groups, in addition to the carbon and hydrogen atoms.

For example, suitable cationic surfactants include the chlorides or bromides of alkyldimethylbenzylammonium salts, alkyltrimethylammonium salts, e.g. cetyltrimethylammonium chloride or bromide, alkyldimethylhydroxyethylammonium chloride, alkyldimethylhydroxyethylammonium chloride or bromide, dialkyldimethylammonium chloride or bromide, alkylpyridinium salts, such as lauryl- or cetylpyridinium chloride, alkylamidoethyltrimethylammonium ether sulfate and compounds with cationic character, such as amine oxides, for example alkylmethylamine oxides or alkylaminoethyldimethylamine oxides. Cetyltrimethylammonium chloride is especially preferred as the cationic surfactant in the composition of the invention.

Foam-breaking Components

The composition in the product according to the invention contains at least one form-breaking agent (B) in order to guarantee a sufficiently rapid foam-breaking of the foam formed immediately after spraying. Suitable foam-breaking agents include $C_1$- to $C_5$-alcohols, oils and silicone oils, e.g. linear or cyclic dimethylsiloxanes with the INCl names dimethicone or cyclomethicone. Non-organic anti-foaming agents, especially those based on physiologically indifferent active ingredients, such as polydimethylsiloxanes/silica, are also suitable. This sort of active ingredient is known under the name Simethicone. These simethicones are mixtures of dimethicones (polydimethylsiloxanes) of an average chain length of from 200 to 350 dimethylsiloxane units and hydrated silica. They can be used in the form of silicone anti-foaming emulsions and are a matter of aqueous emulsions of Simethicones. The $C_2$- to $C_4$-alcohols are especially preferred. The amounts used usually amount to from 1 to a maximum of 30 percent by weight, preferably from 5 to 20 percent by weight. Strong acting anti-foaming agents, such as, the Simethicones, can also be used in small amounts, e.g. from 0.001 to 1, preferably from 0.01 to 0.5 percent by weight.

Solvents

The solvents used in the compositions for the products according to the invention are either water or mixtures of water and one or more organic co-solvents. The content of water amounts to at least 60 percent by weight in relation to the total amount of the composition in the product. Organic co-solvents can be the above-described lower alcohol with one to five carbon atoms, preferably 1 to 4 carbon atoms, such as ethanol and isopropanol. Typical additional organic solvents include, for example, branched or unbranched hydrocarbons, such as pentane, hexane and isopentane, and cyclic hydrocarbons, such as cyclopentane and cyclohexane as well as hydrophilic solvents, such as glycerol, ethylene glycol or propylene glycol. The organic co-solvent can be contained in an amount of up to a maximum of 30 percent by weight, preferably from 0.1 to 15, especially preferably from 1 to 10, percent by weight.

Propellants

The aerosol propellant (E) is preferably contained in the compositions for the products according to the invention in an amount of from 1 to 30, especially preferably from 2 to 20, percent by weight. Lower alkanes, such as n-butane, i-butane, propane, butane or their mixtures and dimethyl-ether or fluorinated hydrocarbons, such as F 152a (1,1-difluoroethane) or F 134 (tetrafluroethane), are suitable. The propellants also include those propellants that are present in gaseous form under pressure, such as $N_2$, $N_2O$ and $CO_2$ and mixtures of those propellants. The lower alkanes and dimethyl ether are especially preferred as those propellants. Especially good spraying and foaming properties are obtained with a mixture of at least one lower alkane, especially butane, and dimethyl ether. A ratio of dimethyl ether to alkane of 2:1 to 8:1 is preferred, while a ratio of 3:1 to 6:1 is particularly preferred.

Additional Polymers

At least one additional weaker hair-fixing polymer and/or at least one thickening polymer are contained in additional embodiments of the compositions in the product according to the invention. The additional weaker fixing polymer can be a polyvinyl pyrrolidone or a polyvinyl pyrrolidone/vinyl acetate copolymer. Thickening polymers include e.g. polyacrylates (INCl name: carbomer). The additional polymer is typically present in an amount of from 0.01 to 15, preferably from 0.5 to 10, percent by weight.

Optional Additive Ingredients

The compositions in the products according to the invention can furthermore contain conventional additive ingredients for hair treatment compositions. These additive ingredients include, e.g. perfumes and fragrances, in an amount of from 0.01 to 0.5 percent by weight; preservatives, especially bactericides and fungicides, in an amount of from 0.01 to 1.0 percent by weight; buffer substances, such as sodium citrate or sodium phosphate, in an amount of from 0.1 to 1.0 percent by weight; hair care materials, such as plant and vegetable extracts, protein and silk hydrolyzates, lanolin derivative compounds, in an amount of from 0.1 to 5 percent by weight; physiologically compatible silicone derivative compounds, e.g. volatile or non-volatile silicone oils or high molecular weight silioxane polymers, in an amount of from 0.05 to 20 percent by weight; light-protective agents; anti-oxidants; radical trapping agents; anti-flaking ingredients, in an amount of from about 0.01 to 2 percent by weight; luster-imparting substances; vitamins; combability-improving agents and de-fatting agents.

Packaging

The compositions in the products according to the invention are filled into pressure-resistant aerosol containers. Conventional packaging or container materials comprising metal, such as aluminum or tin plate, or pressure-resistant plastic materials can be used for the container or packaging. Especially with tin plate, because the composition contains water, a corrosion-resistant interior coating or addition of a known corrosion inhibitor should be considered.

Spray Head

The filled aerosol container is provided with a hair-spray spray head. The spray head is ideally designed so that a comparatively narrow spray angle of less than 40°, preferably at maximum 30°, results to guarantee a desired treatment of individual hair shaft sections. A commercial spray head can be used. Alternatively the spray head can be provided with a tube-like nozzle.

Application

Strands of head hair are taken up by the hand and sprayed with the composition in the product of the invention in the region of the shafts during a typical application. An unstable foam then forms on the sprayed hair shafts. To accelerate the breaking up of the foam and hardening of the polymer film deposited on the hair shafts the sprayed region can be dried with a hair drier. Additional hair sections are treated in a like manner. Finally the hair is brushed as needed.

The following examples should illustrate the subject matter of the invention in further detail.

EXAMPLES

Comparative Tests

The selection of a suitable strongly fixing hair-fixing polymer occurs ideally with the aid of curl retention measurements with a higher humidity in comparison to polyvinyl pyrrolidone and vinylpyrrolidone/vinyl acetate copolymers.

A water wave is produced in each of three white and washed counted hair strand samples (European hair, 16.5 cm long, 100 hairs per strand). The hair stands were weighted with a 10 g weight on their lower end, wound on spiral curlers and treated with 100 microliters respectively of the composition to be tested. The treated hair strands are dried and acclimated overnight at 20° C. and 85% relative humidity. Subsequently the stands were carefully taken from the curlers and weighted with 50 mg on a frame in a climate-controlled chamber or room at 20° C. and 85% relative humidity. The length of the strands is measured prior to suspension and after 23 hours.

The following five polymer solutions A, B, C, D and E, each having a polymer solids content of 5 percent by weight, were tested:

| | | |
|---|---|---|
| A: | 12.5 g | AQUAFLEX ® FX-64 (Isobutylene/Ethylmalimide/ Hydroxyethylmaleimide copolymer, 40% in 27% Water/33% ethanol; ISP) |
| | to 100 g | Ethanol |
| B: | 5 g | AMPHOMER ® (Octylacrylamide/Acrylates/ Butylaminoethyl Methacrylate Copolymer; National Starch) |
| | 3.4 g | Water |
| | 0.86 g | Aminomethylpropanol |
| | to 100 g | Ethanol |
| C: | 25 g | GAFQUAT ® 755N (Polyquaternium-11 20% in water) |
| | to 100 g | Ethanol |
| D: | 10 g | LUVISKOL ® VA37E (PVP/PA Copolymer, 50% in Ethanol; BASF) |
| | 3.4 g | Water |
| | to 100 g | Ethanol |
| E | 5 g | LUVISKOL ® K80 Powder (PVP; BASF) |
| | 3.4 g | Water |
| | to 100 g | Ethanol |

In the comparative test F a water wave without treatment with a polymer solution was produced on a sample of hair strands.

The curl retention W was calculated according to the following relationship:

$$W=\{(L-Lt)/(L-L0)\}\times 100 \text{ in } \%$$

wherein L designates the length of the unwaved strand, Lt designates the length of the waved strand at t=23 hours and L0 designates the length of the waved strand at t=0.

The result are summarized in the following Table I:

TABLE 1

CURL RETENTION FOR DIFFEREVT POLYMER TEST COMPOSITIONS AND COMPARATIVE EXAMPLE

| POLYMER SOLUTION | CURL RETENTION |
|---|---|
| A | 78.7 ± 3.3 |
| B | 78.4 ± 7.5 |
| C | 63.7 ± 8.2 |
| D | 55.4 ± 3.4 |
| E | 58.6 ± 1.2 |
| F | 51.5 ± 2.3 |

Example 1

Aerosol-spray Foam for Hair Shaft Strengthening

| 5.6 g | AQUAFLEX ® FX-64 Isobutylene/Ethylmalimide/ Hydroxyethylmalemide copolymer, 40% in 27% Water/33% ethanol; ISP) |
|---|---|
| 0.15 g | Cetyltrimethylammonium chloride |
| 0.2 g | Laureth-4 |
| 0.2 g | Perfume |
| 10. g | Ethanol |
| to 100 g | Water |

The effective ingredient mixture was filled into an aerosol can made of aluminum with dimethylether/butane (4:1) as propellant in a ratio of 80:20 and the aerosol can was provided with a spray head (DPV APSL 0.025", 0.64 mm).

Example 2

Aerosol-spray Foam for Hair Shaft Strengthening

| 10. g | AQUAFLEX ® FX-64 Isobutylene/Ethylmalimide/ Hydroxyethylmalemide copolymer, 40% in 27% Water/33% ethanol; ISP) |
|---|---|
| 0.1 g | Oramix ® NS10 (Decylglucoside, 55% in water) |
| 0.2 g | Laureth-4 |
| 0.2 g | Perfume |
| 10. g | Ethanol |
| to 100 g | Water |

The effective ingredient mixture was filled into an aerosol can made of aluminum with dimethylether/butane (4:1) as propellant in a ratio of 80:20 and the aerosol can was provided with a spray head (DPV APSL 0.020", 0.51 mm).

Example 3

Aerosol-spray Foam for Hair Shaft Strengthening

| 10. g | AQUAFLEX ® FX-64 Isobutylene/Ethylmalimide/ Hydroxyethylmalemide copolymer, 40% in 27% Water/33% ethanol; ISP) |
|---|---|
| 0.6 g | Vinyl acetate/crotonic acid copolymer |
| 0.1 g | Aminomethylpropanol (95%) |
| 0.1 g | Cetyltrimethylammonium chloride |
| 0.1 g | Laureth-4 |
| 0.2 g | Perfume |
| 20. g | Ethanol |
| to 100 g | Water |

The effective ingredient mixture was filled into an aerosol can made of aluminum with dimethylether/butane (4:1) as propellant in a ratio of 80:20 and the aerosol can was provided with a spray head (DPV APSL 0.020", 0.51 mm).

The disclosure in German Patent Application 100 55 935.2-41 of Nov. 10, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a volume-imparting hair treatment product for strengthening the hair shaft, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment product for strengthening hair shafts of hair, said hair treatment product consisting of a pressure-resistant aerosol container equipped with a spray head and a composition contained in said pressure-resistant container, wherein said composition comprises at least 60% by weight of water;

from 1 to 30% by weight of at least one monovalent alcohol with 1 to 5 carbon atoms, as a foam-breaking agent;

from 0.01 to 5% by weight of a surfactant component;

from 0.1 to 20% by weight of at least one hair-fixing polymer having higher curl retention values than polyvinyl pyrrolidorie, measured after 23 hours at 20° C. and 85% relative humidity; and at least one aerosol propellant wherein said aerosol propellant is a mixture of dimethylether and at least one hydrocarbon selected from the group consisting of propane, n-butane, isobutene and pentane;

whereby a fast-breaking unstable foam is formed when the composition is sprayed by actuating said spray head.

2. The product as defined in claim 1, wherein said surfactant component comprises at least one member selected from the group consisting of nonionic surfactants, anionic surfactants, cationic surfactants and amphoteric surfactants.

3. The product as defined in claim 1, wherein said at least one hair-fixing polymer is selected from the group consisting of polymers containing repeating units of alpha-olefin-N-alkylmaleimide and alpha-olefin N-hydroxyalkylmaleimide; copolymers of alkylacrylamides; copolymers of alkylamino-alkylmethacrylates and two or more monomers selected from the group consisting of acrylic acid, methacrylic acid, acrylic acid esters and methacrylic acid esters; copolymers of vinylpyrrolidone and quaternarized dialkylamino-alkylacrylates; copolymers of vinyl acetate and crotonic acid; copolymers of acrylamides and one or more monomers selected from the group consisting of acrylic acid, methacrylic acid, acrylic acid esters and methacrylic acid esters; terpolymers of vinyl pyrrolidone, vinyl caprolactam and basic acrylamide monomers; and copolymers of two or more different monomers selected from the group consisting of acrylic acid, methacrylic acid, acrylic acid esters and methacrylic acid esters.

4. The product as defined in claim 1, wherein said at least one hair-fixing polymer is a copolymer of isobutylene-N-ethylmaleimide and isobutylene-N-hydroxyethylmaleimide.

5. The product as defined in claim 1, wherein said dimethylether and said at least one hydrocarbon are present in a weight ratio of said dimethylether to said at least one hydrocarbon of 2:1 to 8:1.

6. The product as defined in claim 2, wherein said surfactants comprise surface-active compounds that form a foam with a foam height of at least 1 cm in a Ross-Miles test at 20° C.

7. The product as defined in claim 1, wherein said composition contains at least one thickener or additional hair-fixing polymer.

8. The product as defined in claim 7, wherein said at least one thickener or additional hair-fixing polymer is selected from the group consisting of polyvinyl pyrrolidone, polyvinyl pyrrolidone/vinyl acetate copolymers and polyacrylates.

9. A hair treatment product for strengthening hair shafts of hair, said hair treatment product consisting of a pressure-resistant aerosol container equipped with a spray head having a spraying angle of less than 40° and a composition contained in said pressure-resistant container, wherein said composition comprises at least 60% by weight of water;

from 1 to 30% by weight of at least one monovalent alcohol with 1 to 5 carbon atoms, as a foam-breaking agent;

from 0.01 to 5% by weight of a surfactant component;

from 0.1 to 20% by weight of at least one hair-fixing polymer having higher curl retention values than polyvinyl pyrrolidone, measured after 23 hours at 20° C. and 85% relative humidity; and at least one aerosol propellant wherein said aerosol propellant is a mixture of dimethylether and at least one hydrocarbon selected from the group consisting of propane, n-butane, isobutene and pentane;

whereby a fast-breaking unstable foam is formed on a selected section of the hair including the hair shafts, when the composition is sprayed by actuating said spray head.

10. The product as defined in claim 9, wherein said surfactant component comprises at least one surfactant that forms a foam having a foam height of at least 1 cm in a Ross-Miles test at 20° C.

11. The product as defined in claim 9, wherein said at least one hair-fixing polymer is selected from the group consisting of polymers containing repeating units of alpha-olefin-N-alkylmaleimide and alpha-olefin N-hydroxyalkyl-maleimide; copolymers of alkylacrylamides; copolymers of alkylaminoalkyl-methacrylates and two or more monomers selected from the group consisting of acrylic acid, methacrylic acid, acrylic acid esters and methacrylic acid esters; copolymers of vinylpyrrolidone and quaternarized dialkylaminoalkylacrylates; copolymers of vinyl acetate and crotonic acid; copolymers of acrylamides and one or more monomers selected from the group consisting of acrylic acid, methacrylic acid, acrylic acid esters and methacryhc acid esters; terpolymers of vinyl pyrrolidone, vinyl caprolactam and basic acrylamide monomers; and copolymers of two or more different monomers selected from the group consisting of acrylic acid, methacrylic acid, acrylic acid esters and methacrylic acid esters.

12. A method for increasing volume of a hairdo by selectively fixing or strengthening hair shafts, said method comprising the steps of:

a) taking up hair strands by hand;

b) after the hair strands are taken up, subsequently applying a hair treatment composition selectively to the hair shafts of said hair strands taken up by hand so as to form a fast-breaking foam on the hair shafts;

c) after the applying of step b), drying the hair shafts by means of a hair drying apparatus while holding the hair strands upwards;

wherein said composition comprises at least 60% by weight of water; from 1 to 30% by weight of at least one monovalent alcohol with 1 to 5 carbon atoms, as a foam-breaking agent; from 0.01 to 5% by weight of a surfactant component; from 0.1 to 20% by weight of at least one hair-fixing polymer having higher curl retention values than polyvinyl pyrrolidone, measured after 23 hours at 20° C. and 85% relative humidity and at least one aerosol propellant wherein said aerosol propellant is a mixture of dimethylether and at least one hydrocarbon selected from the group consisting of propane, n-butane, isobutene and pentane.

13. The method as defined in claim 12, wherein the applying is performed by spraying said composition by means of a spray head having a spraying angle of less than 40° so that only a section of hair including the hair shafts is provided with said foam.

14. The method as defined in claim 12, wherein said surfactant component comprises at least one surfactant that forms a foam having a foam height of at least 1 cm in a Ross-Miles test at 20° C.

* * * * *